United States Patent [19]
Bailey et al.

[11] Patent Number: 5,818,049
[45] Date of Patent: Oct. 6, 1998

[54] INFRARED GAS SPECTROMETER HAVING A LID ASSEMBLY WITH AN INTEGRATED CHOPPER AND CHOPPER MOTOR

[75] Inventors: William D. Bailey, Arvada; G. Lamar Kirchheval, Westminster, both of Colo.

[73] Assignee: Ohmeda Inc., Liberty Corner, N.J.

[21] Appl. No.: 920,995

[22] Filed: Aug. 29, 1997

[51] Int. Cl.⁶ ..................................................... G01N 21/35
[52] U.S. Cl. ........................ 250/343; 250/351; 250/233
[58] Field of Search ..................................... 250/232, 233, 250/343, 345, 351, 239, 339.13; 356/437; 600/529, 532, 543, 310

[56] References Cited

U.S. PATENT DOCUMENTS

| | | | |
|---|---|---|---|
| 3,897,153 | 7/1975 | Keenan et al. ........................... | 250/345 |
| 5,585,635 | 12/1996 | Graham .................................... | 250/343 |
| 5,731,581 | 3/1998 | Fischer et al. ...................... | 250/339.13 |
| 5,731,583 | 3/1998 | Bailey et al. ........................... | 250/343 |

*Primary Examiner*—Edward J. Glick
*Assistant Examiner*—Darren M. Jiron
*Attorney, Agent, or Firm*—Roger M. Rathbun

[57] ABSTRACT

A respiratory gas monitor for measuring the concentration of certain gases in a respiratory gas stream has a compact and unitary lid assembly having an integral low-profile motor and a cylindrical infrared light beam chopper. The lid assembly also contains a motor position sensor and flex circuit for passing electrical signals through epoxy sealed orifices in the lid to a processing and control unit in the monitor. The flexible circuit uses releasable connectors to facilitate removal of the monitor from an external controller and the removal of the lid assembly from the bottom portion of the monitor.

12 Claims, 3 Drawing Sheets

INFRARED GAS SPECTROMETER HAVING A LID ASSEMBLY WITH AN INTEGRATED CHOPPER AND CHOPPER MOTOR

FIELD OF THE INVENTION

This invention relates to gas spectrometers used for measuring the concentration of pre-defined components of a gas sample, particularly those spectrometers using an infrared source to transmit light through a sample gas containing oxygen, carbon dioxide and anesthetic gas agents. Such spectrometers, often referred to as anesthetic gas monitors, are used in hospitals to monitor the administration of oxygen and anesthesia provided to patients as well as to monitor the level of carbon dioxide in the patient's breath.

BACKGROUND OF THE INVENTION

Infrared gas spectrometers are utilized in a variety of industrial and medical applications to monitor the presence and concentration of one or more pre-defined components in a gas sample. Typically, infrared light having a known spectral content is transmitted through a sample of the gas being analyzed and the transmitted light is detected at a number of different center wavelengths providing detected light intensities at these various center wavelengths. By processing the detected light intensities using known light absorption characteristics of the gas components under analysis, the concentrations of the individual gas components can be determined. For example, a particular gas component may be characterized by an absorption band at a particular wavelength or wavelength range. To monitor multiple gas components, some spectral gas analyzers employ multiple radiation sources, multiple optical filters and/or multiple radiation detectors.

In addition to providing a gas spectrometer having a high degree of accuracy in the analysis of the components in a gas sample, it is also desirable to limit the number of active components such as radiation source and receiver components, thereby simplifying spectrometer design, reducing costs, reducing power requirements and heat production, and increasing reliability.

Moreover, for many applications where space is limited, it is desirable to reduce spectrometer size. Particularly in the clinical hospital setting where space is at a premium it is important that the spectrometer, in the form of an anesthetic gas monitor or monitoring component of a multi-parameter system, be of a low profile and of diminutive proportions in order to fit into as many clinical settings and existing modular systems as possible.

An additional consideration is the serviceability of the monitor. In order to enhance serviceability a monitor should have a minimal number of components which can fail and should have easily replaceable sub-assemblies which can then be quickly replaced and then returned for servicing or repair.

SUMMARY OF THE INVENTION

In view of the foregoing, a primary object of the present invention is to provide a gas spectrometer having a minimal number of components in order to decrease cost and improve reliability.

A related objective is to provide a gas spectrometer which has a low profile so as to minimize space requirements and so as to be adaptable for use with the greatest number of existing multiple parameter monitoring platforms.

A further objective is to provide a gas spectrometer having an easily separable modular component for ease of servicing and off-site testing and repair.

A still further objective is to provide a gas spectrometer having an internal cavity which is sealed from external contamination so as to minimize the contamination of the optical system components housed therein.

To achieve such objectives and realize advantages, the gas spectrometer of the present invention uses a lid assembly having an integrated low-profile motor with an integrated cylindrical chopper, a chopper motor position sensor and a flexible connector for passing electrical connection through the lid assembly and on to the spectrometer circuitry.

Such a lid may be used in an infrared gas spectrometer as described in CO-pending U.S. patent application Ser. No. 08/606,371 which is hereby incorporated by reference. Such a spectrometer includes a chamber for containing a gas sample to be analyzed, a means for transmitting a polychromatic radiation beam through the gas sample and a reference gas, a means for filtering the polychromatic beam to yield two or more wavelength band portions, and a means for separately detecting the wavelength band portions to provide information based on the intensity of radiation in the corresponding wavelength bands. The filtering means preferably includes a linear variable filter for providing varying wavelength response characteristics across the width of the beam. In order to separately detect the intensity of the wavelength band portions, the detector means preferably comprises an array of detector elements for providing a signal indicative of the intensity of the radiation passing through a sample gas at a plurality of wavelengths.

An optical chopper is provided to permit selective transmission of radiation from a single source via two optical paths according to a selected duty cycle. Each of the optical paths is defined in part by an optical element, such as a lens or mirror, that receives radiation from the source. The optical chopper includes a moveable radiation mask having at least one opening to allow passage of radiation. The chopper is preferably provided in the form of a rotatable cylinder positioned around the source. The operation of the chopper can be coordinated with cycling of a detector to achieve a desired sampling rate or duty cycle.

The spectrometer includes an infrared radiation source disposed within a rotatable cylindrical chopper having at least one slit formed in a side wall thereof. Due to rotation of the cylindrical chopper, radiation passing through the slit(s) is alternately transmitted on separate sample and reference paths. Each path includes a spherical mirror for collecting radiation from the source to form a converging beam. On the sample path, the converging beam passes through a chamber containing a circulated sample of respiratory and anesthetic gases. The converging beam of the reference path passes through a chamber that contains a known gaseous composition. The optical paths are configured so that each of the converging beams passes through a linear variable filter and impinges on a single column detector array upon exiting the respective chambers. The readout from the detector array provides information concerning multiple components of the gas sample.

The present invention reduces the number and size of active spectrometer components while allowing for dual optical path, polychromatic gas analysis of anesthetic/respiratory gases by placing a low-profile "pancake" motor in the lid assembly which closes the housing of the gas spectrometer. The motor is used to rotate the cylindrical chopper. In the preferable embodiment the motor is positioned on the inside of the lid assembly.

The lid assembly also contains a motor position sensor for providing feedback to the electronics controlling the chopper motor. A flexible circuit allows for passage of electrical control signals from an external source to internal processing components.

The foregoing design results in a gas spectrometer having a reduced height, improved sealability, easier serviceability and increased reliability as will be better understood after review of the detailed description to follow.

DETAILED DESCRIPTION OF THE DRAWINGS

Figure 1:
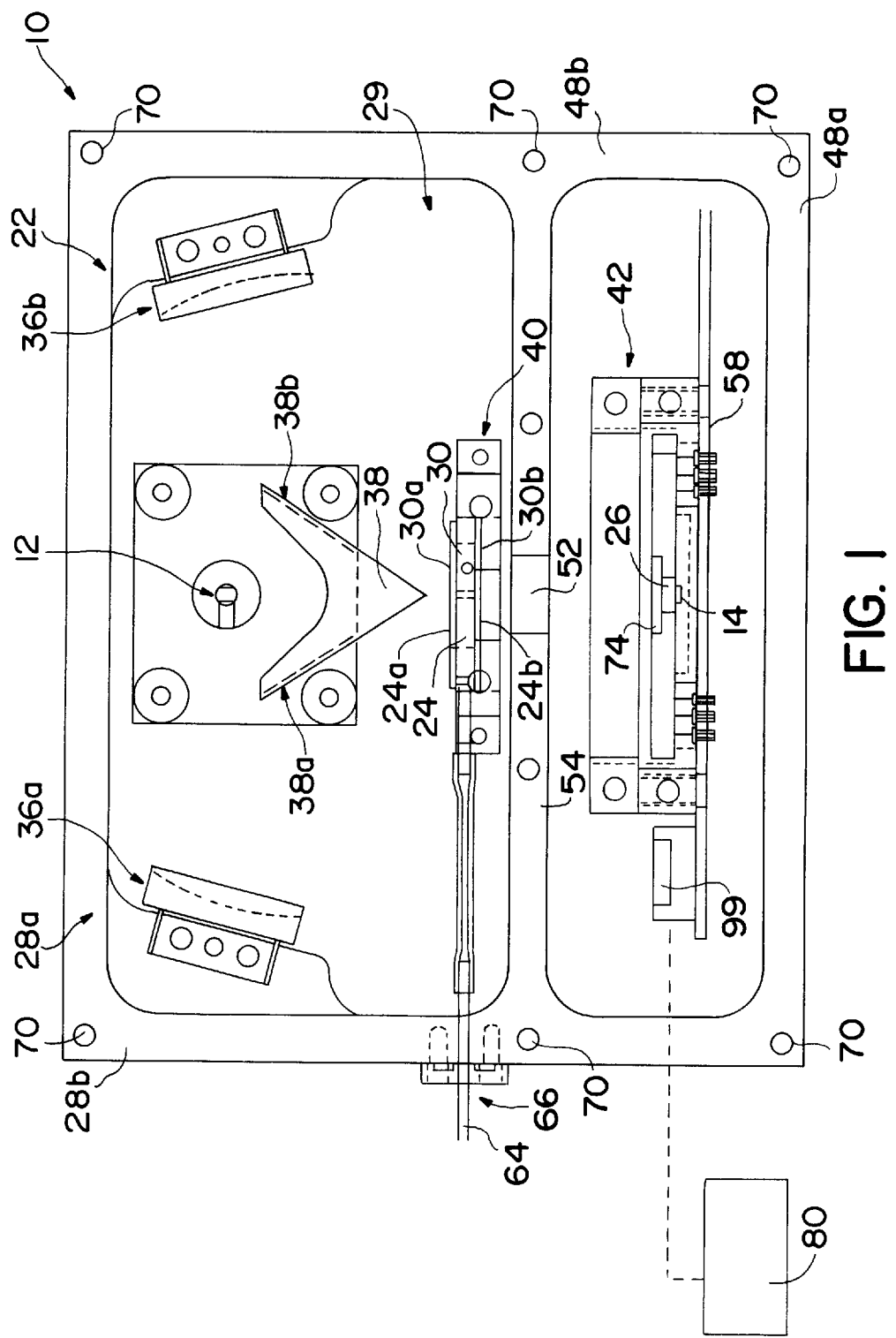
FIG. 1 is a top view of a bottom portion of a spectrographic respiratory gas monitor according to the present invention with external components schematically represented.
Figure 2:
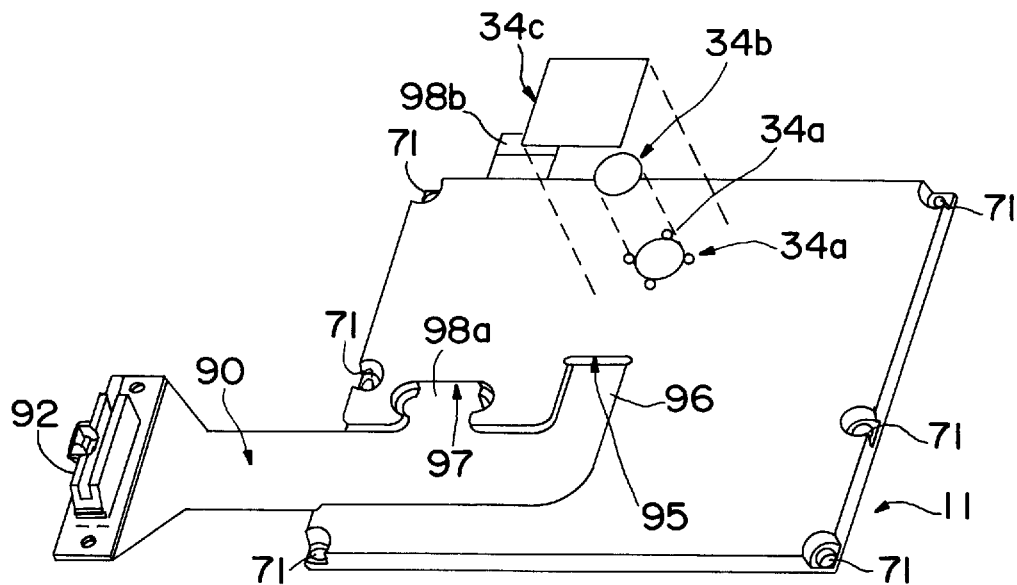
FIG. 2 is an elevational view of the top-side of an embodiment of a lid assembly according to the present invention.
Figure 3:
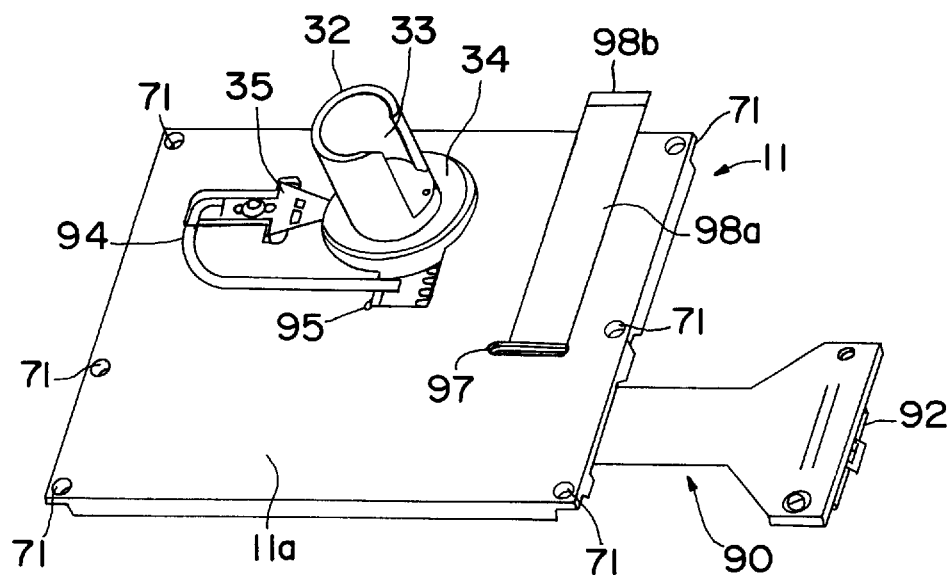
FIG. 3 is an elevational view of the bottom side of an embodiment of a lid assembly according to the present invention.
Figure 4:
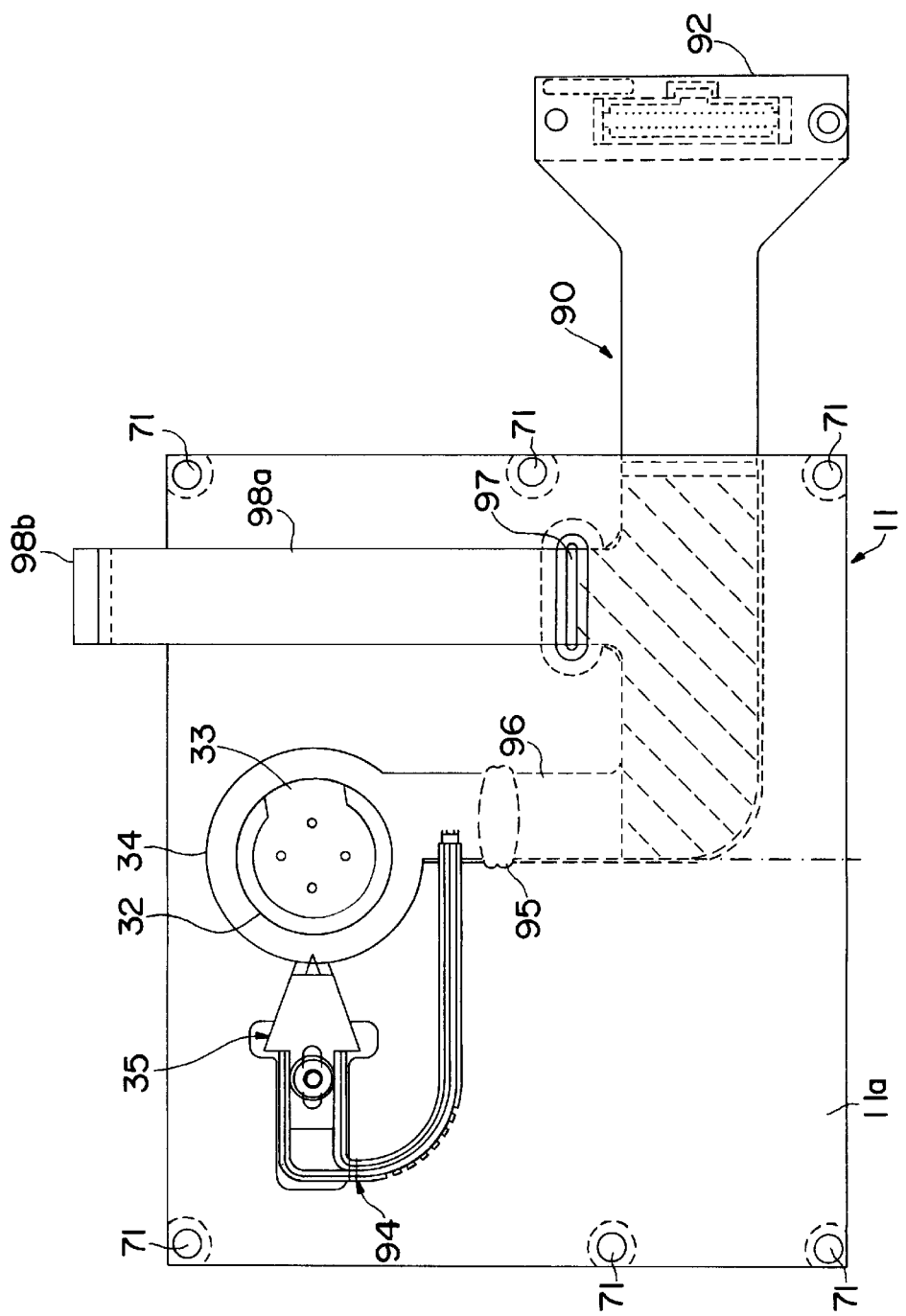
FIG. 4 is a top view of the bottom side of an embodiment of a lid assembly according to the present invention.

In FIG. 1 an implementation of the bottom portion 10 of a gas spectrometer is illustrated. The bottom portion 10 has a bottom 29 and four wall sections 28a and 28b and 48a and 48b as well as an internal partition wall 54. In FIGS. 2–4 an implementation of the top portion 11 is depicted which is designed to mate with and attach to bottom portion 10 through threaded screw fittings 70 and screw holes 71.

The gas spectrometer includes an upstanding infrared radiation source 12 positioned within a concentric, rotatable, cylindrical beam chopper 32. The cylindrical beam chopper 32 is attached to and rotated by low-profile motor 34 and extends downwardly from top portion 11 to partially enclose infrared radiation source 12. Low-profile motor 34 is mounted either on the bottom face 11a of top portion 11 or is mounted into a well which may extend either substantially through or entirely through top portion 11 thereby minimizing the vertical space requirement for the spectrometer.

In FIG. 1, in addition bottom portion 10 of a gas spectrometer according to the present invention houses two spherical mirrors 36a, 36b, a flat mirror block 38 having flat mirrors 38a, 38b, a dual gas chamber member 40 having a sample gas chamber 24 and a reference gas chamber 30, and a filter/detector assembly 42 having polychromatic filter 26 and detector 14.

Infrared source 12 emits radiation which, by virtue of the rotation of the chopper 32, results in the alternate impingement of infrared light beams on spherical mirrors 36a and 36b, respectively. In turn, convergent beams respectively reflect off spherical mirrors 36a and 36b and impinge on flat mirror elements 38a and 38b, respectively. The reflected infrared beams then irradiate sample gas chamber 24 and reference gas chamber 30, respectively, before impinging on detector array 14.

The illustrated source 12 irradiates sample gas chamber 24 and reference gas chamber 30 with radiation encompassing a characteristic absorption band of at least one respiratory/anesthetic component of interest. Although various wavelengths or spectra can be employed including infrared (IR), visible and ultraviolet wavelength ranges, the illustrated source 12 is a polychromatic (black body) IR source transmitting radiation encompassing, for example, radiation in about the 4–12 micrometer wavelength range, which includes strong absorption bands of several respiratory/anesthetic components (e.g., within the 7–10 micrometer range).

The source 12 being mounted within rotatable cylindrical beam chopper 32 with aperture 33 alternately transmits radiation from source 12 through the sample gas chamber 24 and reference gas chamber 30. Cylindrical beam chopper 32 also contains, to an extent, heat generated by the source 12. The cylindrical chopper 32 is rotated via chopper motor 34 which is driven by external power and control circuitry 80 which is connected to the chopper motor 34 via portion 96 of flexible circuit 90. Motor position sensor 35 is mounted near the periphery of chopper motor 34 and is a well known reflective emitter-detector type sensor which sends feedback to the processing unit 80 via flex circuit 90 based on the sensed rotation of the armature components of chopper motor 34. This enables the external power and control circuitry 80 to control the rotation of the chopper 32 and, therefore, the timing of the illumination of sample gas chamber 24 and the reference gas chamber 30.

Flexible circuit 90 connects the filter/detector assembly 42 to the lid assembly 11 via flex portion 98a whose end 98b mates to a zero insertion force (ZIF) type connector 99. Additionally, flexible circuit 90 connects the filter/detector assembly 42, motor position sensor 35 (via additional pigtail wires 94) and motor 34 to external power and control circuitry 80 (shown schematically in FIG. 1) via connector 92. These two connectors 92 and 98b enable the quick detachment of the lid assembly 11 from the filter/detector assembly 42 and external power and control circuitry 80 greatly enhancing serviceability of the spectrometer.

Portion 96 and portion 98 of flexible circuit 90 are placed through holes 95 and 97 respectively and an epoxy adhesive is used to create a gas impermeable barrier so as to create a sealed environment when top portion 11 and bottom portion 10 are put together and sealed. Top portion 11 is placed on bottom portion 10 so that screw holes 71 in top portion 11 align with threaded screw holes 70 in bottom portion 10. A gasket (not shown) and vacuum grease are used to insure a gas impermeable seal between top portion 11 and bottom portion 10.

After illuminating sample gas chamber 24 and reference gas chamber 30, which are sealed chambers having opposing transparent walls 24a and 24b and 30a and 30b, respectively, the infrared radiation passes through transparent window 52 in internal partition 54. The infrared radiation then impinges on filter 26 and finally impinges upon detector array 14 both part of filter/detector assembly 42. A band pass filter 74 may be positioned in front of the polychromatic filter 26 to selectively pass radiation in the wavelength range of interest. In addition, a separate filter 75 (not shown), such as a sapphire $CO_2$ filter, may be positioned in adjacent, stacked relation to the polychromatic filter 26 for use in analyzing a specific component. Filter 26, as discussed above, is a polychromatic filter including multiple sections that are selective for multiple wavelengths or wavelength ranges of interest. In this regard, the filter 26 can be formed as an array of bandpass filters arranged side-by-side in the beampaths. More preferably, the filter comprises a linear variable filter that provides substantially linearly varying wavelength response characteristics across a beamwidth. Such a filter can be formed by depositing a stack of alternating high and low index of refraction materials on a filter substrate, where the stack layers are tapered in a controlled manner to yield the desired wavelength response variation. The illustrated filter provides substantially linearly varying wavelength response across, for example, the approximately 7–10 micrometer wavelength range.

The infrared radiation detector array 14 includes a single column of pyroelectric or heat sensitive elements and is supported by a detector board 58 carrying the circuitry for reading out the detector array 14, e.g., serial clocking circuits. The read out clocking of the detector array 14 can be readily coordinated with the chopper 32 rotation rate to provide alternate sample and reference values. In this regard, the 180° spacing of the spherical mirrors 36*a* and 36*b* relative to the source 12 allows for convenient interval clocking. Such coordination may be accomplished, for example, by indexing the read out clocking to pulses from motor position sensor 35 associated with the motor 34 and chopper 32. It will thus be appreciated that specific elements of the array 14 are associated with specific wavelength bands of filter 26. A polychromatic analysis of an incident beam can therefore be obtained by correlating the output from a particular element, or group thereof, and the associated wavelength band. This information can be used by the external power and control circuitry 80 (FIG. 1) to determine gaseous composition information pertaining to multiple gaseous components in the sample and reference gases. Gas inlet tubes 64 and an associated housing pass-through 66 supply a sample gas to the sample gas chamber 24. Gas inlet tubes may also be arranged so that they exit the base of bottom portion 10 rather than through the depicted side ports.

Numerous additional embodiments and variations of the invention will be apparent to those skilled in the art and are intended to be within the scope of the present invention, as defined by the following claims.

What is claimed is:

1. A respiratory gas monitor for determining the concentration of one or more pre-defined components of a respiratory gas sample, comprising:

a bottom portion having a bottom panel and four walls extending therefrom and a top portion mated to said bottom portion;

wherein said bottom portion comprises:

an infrared radiation source for generating a plurality of beams of infrared radiation;

a sample gas chamber having opposing transparent walls and being positioned for receiving a respiratory gas sample;

a reference gas chamber having opposing transparent walls and containing a reference gas sample;

an optical assembly for directing said plurality of beams of infrared radiation through said transparent walls of said sample gas chamber onto a filter/detector assembly;

said filter/detector assembly for receiving said plurality of beams of infrared radiation which pass through said transparent walls of said sample gas chamber and said reference gas chamber for generating a signal indicative of the concentration of said one or more pre-defined components of said respiratory gas sample and said reference gas sample;

external power and control circuitry for generating a concentration measurement for said pre-defined components using said signals generated by said filter/detector assembly;

and, wherein said top portion comprises:

a substantially planar surface having a thickness;

a motor disposed on said surface;

a substantially cylindrical chopper axially and rotatably connected to said motor for selectively illuminating said sample gas chamber and said reference gas chamber;

a motor position sensor disposed substantially adjacent said motor for providing said control circuitry with a signal indicative of the angular position of said chopper motor;

and a connector circuit for releasably connecting said motor position sensor and said chopper motor to said control circuitry.

2. A respiratory gas monitor according to claim 1 wherein said top and bottom portions provide a housing sealed to external contaminants.

3. A respiratory gas monitor according to claim 1 wherein said chopper motor is a low-profile motor.

4. A respiratory gas monitor according to claim 3 wherein said chopper motor is at least partially housed within said thickness of said substantially planar surface.

5. A respiratory gas monitor according to claim 1 wherein said connect or circuit is a substantially planar flexible circuit.

6. A respiratory gas monitor according to claim 1 wherein said connector circuit is partially disposed on one side of said substantially planar surface and passes through apertures in the thickness of said surface.

7. A respiratory gas monitor according to claim 6 wherein epoxy is used around said connector circuit to seal said apertures in said planar surface.

8. A lid assembly for a respiratory gas monitor comprising;

a substantially planar lid having a thickness;

a motor fixedly attached to one side of said lid;

a hollow, cylindrical light-beam chopper having at least one aperture partially disposed along said cylinder, said chopper connected to said motor for axial rotation of said chopper;

a motor position sensor disposed substantially adjacent said motor for providing a signal indicative of the angular position of said chopper motor;

and a connector circuit for releasably connecting said motor position sensor and said chopper motor to a filter/detector assembly and an external controller.

9. A lid assembly for a respiratory gas monitor according to claim 8 wherein said chopper motor is a low-profile motor.

10. A lid assembly for a respiratory gas monitor according to claim 9 wherein said chopper motor is at least partially housed within said thickness of said substantially planar lid.

11. A lid assembly for a respiratory gas monitor according to claim 8 wherein said connector circuit is a substantially planar flexible circuit having a first connector and a second connector wherein said first connector is adapted to connect said chopper motor and said motor position sensor to said filter/detector assembly and said second connector is adapted to connect said filter/detector assembly and said chopper motor and said motor position sensor to said external controller.

12. A lid assembly for a respiratory gas monitor according to claim 11 wherein the first connector is a zero insertion force connector.

\* \* \* \* \*